(12) United States Patent
Burgos et al.

(10) Patent No.: US 7,462,742 B2
(45) Date of Patent: Dec. 9, 2008

(54) IN SITU OR ONE-POT HYDROGENATION AND REDUCTIVE AMINATION PROCESS

(75) Inventors: Alain Burgos, Les Ponts-de-Ce (FR); Jacques Tonnel, Beaucouze (FR); Valéry Dambrin, Saint Genis-Laval (FR); Denis Lucet, Rueil-Malmaison (FR); Patricia Poirier, Saint Clement de la Place (FR)

(73) Assignee: Zach System, Avrille (FR)

( * ) Notice: Subject to any disclaimer, the term of this patent is extended or adjusted under 35 U.S.C. 154(b) by 0 days.

(21) Appl. No.: 11/656,573

(22) Filed: Jan. 23, 2007

(65) Prior Publication Data

US 2008/0125606 A1 May 29, 2008

(30) Foreign Application Priority Data

Nov. 23, 2006 (FR) .................................. 06 55082

(51) Int. Cl.
C07C 209/00 (2006.01)
(52) U.S. Cl. ....................................... 564/316; 568/448
(58) Field of Classification Search ...................... None
See application file for complete search history.

(56) References Cited

U.S. PATENT DOCUMENTS

| 5,043,466 A | 8/1991 | Shepard | |
| 6,350,912 B1* | 2/2002 | Chavan et al. | 564/336 |
| 2005/0033088 A1* | 2/2005 | Reguri et al. | 564/141 |

FOREIGN PATENT DOCUMENTS

| EP | 0 112 669 A2 | 7/1984 |
| EP | 1 238 965 B1 | 6/2005 |
| WO | WO 02/50017 A1 | 6/2002 |

OTHER PUBLICATIONS

Yardley et al., "2-Phenyl-2-(1-hydroxycycloalkyl)ethylamine Derivatives: Synthesis and Antidepressant Activity." *J. Med. Chem.* 33(1990): 2899-2905.

* cited by examiner

*Primary Examiner*—Samuel A Barts
(74) *Attorney, Agent, or Firm*—Merchant & Gould P.C.

(57) ABSTRACT

An in situ or one-pot process for the preparation of the compounds of formula (I) uses a compound of general formula (I):

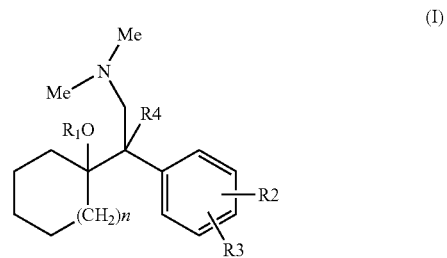

and includes:
a) the hydrogenation of a nitrile group of the compound of general formula (II):

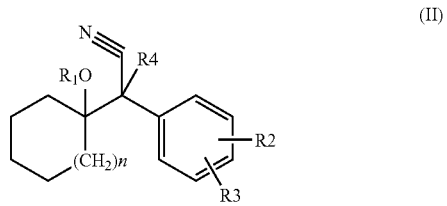

in which $R_1$ to R4 are especially H or alkyl and n varies from 0 to 4, in the presence of a hydrogenation catalyst, a methylating agent and an organic acid as solvent, and at a temperature Ta below the initiation temperature of a reductive amination reaction, to give a primary amine from the nitrile group; and
b) the reductive amination of the primary amine in the presence of hydrogen, at a temperature Tb above Ta, to give the dimethylated amine of general formula (I) by activation of the methylating age.

16 Claims, No Drawings

IN SITU OR ONE-POT HYDROGENATION AND REDUCTIVE AMINATION PROCESS

The present invention relates to a novel in situ or one-pot process for the preparation of the compounds of formula (I). More particularly, the invention relates to a novel process for the preparation of venlafaxine of formula (I)A.

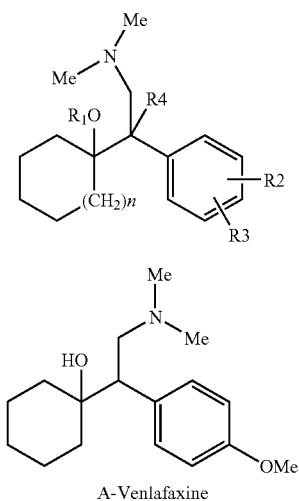

A-Venlafaxine

STATE OF THE ART

The literature discloses two-step processes for the synthesis of the compounds of formula (I) from a compound derived from a nitrile, by carrying out a hydrogenation or reduction reaction of the nitrile group to give a primary amine, followed by a reductive amination reaction of the primary amine, by the Eschweiler-Clarke process, in the presence of formaldehyde and formic acid, to give the N,N-dimethyl group.

1—Patent WO 02/50017 to the Ciba Specialty Chemicals Holding group claims a hydrogenation process in the presence of a nickel-based or cobalt-based catalyst, particularly in the presence of Raney nickel, at a hydrogen pressure of between 1 and 200 bar, to give the primary amine with a yield of 91%. This amine is then used in a reductive amination reaction by the Eschweiler-Clarke process.

2—Patent US 2005/0033088 to the Reddy's group claims a hydrogenation process in the presence of a palladium catalyst, particularly palladium-on-charcoal, at a hydrogen pressure of between 5 and 25 kg/cm$^2$ (5 and 25 bar), in an organic acid such as formic acid, acetic acid or propionic acid, to give the primary amine with a yield of 45-55%. As above, this amine is then used in a reductive amination reaction by the Eschweiler-Clarke process.

3—Patent EP 1238965 to the Council of Scientific and Industrial Research and the article Tetrahedron Letters, 2004, 45, p. 7291 describe a one-step process for the preparation of venlafaxine by carrying out a hydrogenation reaction catalyzed by Raney nickel in methanol, and a reductive amination reaction.

The compound venlafaxine is then obtained with a yield of 30%.

According to the prior art, these hydrogenation processes for obtaining the compounds of formula (I) are performed in two steps including the isolation of the primary amine, which results in a loss of efficiency from a technical point of view and an economic cost.

According to the prior art, these processes use formaldehyde in solution, which involves health and safety constraints when handling this solution in industrial quantities.

According to the prior art, the use of Raney nickel as a catalyst in the hydrogenation reaction requires a chemical pretreatment. This treatment adds a constraint when carrying out the reaction.

Furthermore, for an efficient catalytic activity, the amount of nickel used relative to the starting compound is very high. In fact, as cited in patent WO 02/50017, the amount of catalyst relative to the starting material is in a proportion by weight of 1.6:1.

According to the prior art, the one-step process is still at the experimental stage because the low yield makes it inapplicable to industrial production.

OBJECTS OF THE INVENTION

One main object of the present invention is to develop a process for obtaining the compounds of formula (I) with a high yield by carrying out a hydrogenation reaction and a reductive amination reaction in situ, or in one pot, starting from a compound carrying a nitrile group.

More specifically, another main object of the present invention is to develop a process for obtaining venlafaxine with a yield of 90% by carrying out a hydrogenation reaction of a nitrile and a reductive amination reaction in situ, or in one pot, starting from a compound carrying a nitrile group.

DESCRIPTION OF THE INVENTION

Venlafaxine is a pharmaceutical active principle claimed by the Wyeth group in patent number EP 112669. This active principle is used in the treatment of depression, anxiety, hyperactivity, etc.

The Applicant has developed an in situ or one-pot process for the synthesis of the compounds of formula (I) from the compounds of formula (II), said process being described by scheme S below:

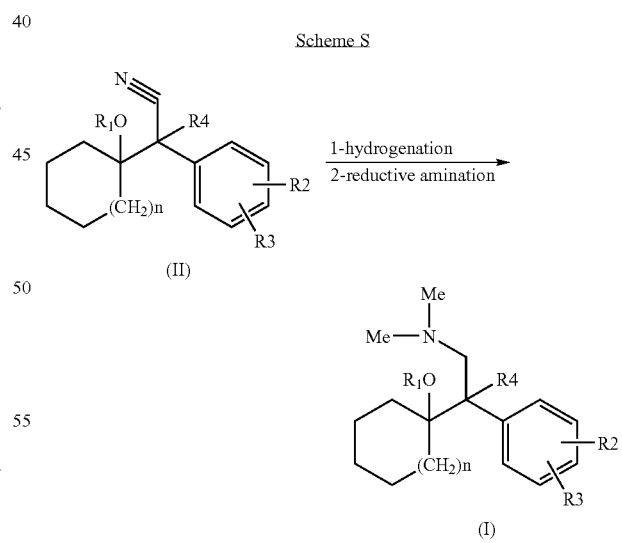

in which $R_1$ is a hydrogen atom, a linear or branched $C_{1-6}$-alkyl, a formyl, a $C_{2-7}$-alkanoyl, a benzyl (—$CH_2C_6H_5$), a tetrahydrofuranyl, an alkylsilyl or arylsilyl, or a protective group for an oxygen atom, Gp, such as those known in the literature and described in the book "Protective Groups in Organic Synthesis, 1999, 3rd edition, by the authors Theodora W. Greene and Peter G. M. Wuts, published by John Wiley & Sons";

R2 and R3 independently are a hydrogen atom, a linear or branched $C_{1-6}$-alkyl, a $C_{1-6}$-alkoxy (—OAk), a $C_{1-7}$-alkanoyloxy (—OC(O)Ak), a $C_{1-6}$-thioalkyl (—SAk), a halogen atom (Cl, Br, F), a trifluoromethyl (—$CF_3$), an "oxy" group where the oxygen atom is bonded to a protective group (—OGp), Gp being as defined above, or a substituted or unsubstituted $C_{6-10}$-aryloxy (—OAr), or R2 and R3 together form a methylenedioxy (—OR2R3O—);

R4 is a hydrogen atom or a linear or branched $C_{1-6}$-alkyl; and n is the integer 0, 1, 2, 3 or 4, characterized in that it comprises:

a) the hydrogenation of a nitrile group of the compound of general formula (II):

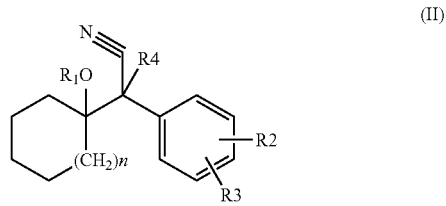

(II)

in which $R_1$, R2, R3, R4 and n are as defined above, in the presence of a hydrogenation catalyst, a methylating agent and an organic acid as solvent, and at a temperature Ta below the initiation temperature of a reductive amination reaction, to give a primary amine from the nitrile group; and b) the reductive amination of the primary amine in the presence of hydrogen, at a temperature Tb above Ta, to give the dimethylated amine of general formula (I) by activation of the methylating agent.

In one advantageous embodiment, the process is characterized in that the compound of formula (I) is such that $R_1$ is a hydrogen atom, R2 is a methoxy group in the para position, R3 and R4 are a hydrogen atom and n is equal to 1.

More precisely, the invention relates to a process for the synthesis of venlafaxine, the compound of formula (I)A, from the compound of formula (II)A according to scheme S-A below:

Scheme S-A

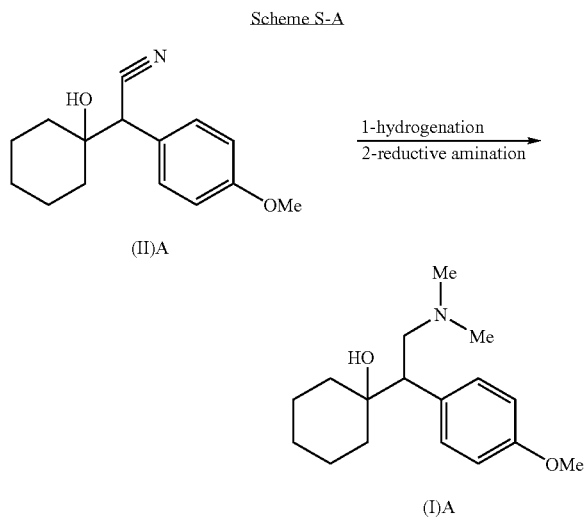

a) Hydrogenation Reaction

In one advantageous embodiment of the process of the invention described by scheme S-1 and scheme S-A1, the catalyst used is a supported or unsupported catalyst based on palladium, platinum or nickel.

By way of a non-limiting example, catalysts which may be mentioned are palladium, palladium-on-carbon, palladium hydroxide (Pd(OH)$_2$), palladium-on-alumina, palladium-on-carbonate, palladium-on-sulfate, platinum, platinum-on-carbon, platinum-on-alumina, platinum dioxide (PtO$_2$), nickel, nickel-on-alumina, nickel-on-silica and Raney nickel.

Preferably, the catalyst used is palladium supported on carbon (Pd/C).

In one advantageous embodiment of the process of the invention described by scheme S-1 and scheme S-A1, the process is carried out in an aqueous solution of an organic acid such as formic acid, acetic acid or propionic acid. Preferably, the organic acid is acetic acid.

In one advantageous embodiment of the process of the invention described by scheme S-1 and scheme S-A1, the methylating agent used is selected from formaldehyde, paraformaldehyde, linear polyoxymethylenes, cyclic polyoxy-methylenes (1,3,5-trioxane, 1,3,5,7-tetraoxane) and polyoxymethylene diacetates. Preferably, the methylating agent used is paraformaldehyde in a solid form.

In one advantageous embodiment of the invention described by scheme S-1 and scheme S-A1, the hydrogenation reaction is carried out at a temperature Ta of between 5 and 25° C., preferably of between 5 and 15° C.

In one advantageous embodiment of the invention described by scheme S-1 and scheme S-A1, the amount of catalyst used relative to the product is between $\frac{1}{1000}$ and $\frac{1}{10}$, preferably between $\frac{1}{100}$ and $\frac{5}{100}$ and particularly preferably between $\frac{1}{100}$ and $\frac{2}{100}$, expressed in mol of metal/mol of product.

In one advantageous embodiment of the invention described by scheme S-1 and scheme S-A1, the hydrogenation reaction is carried out at a hydrogen pressure of between 1 and 30 bar, preferably of between 5 and 15 bar.

In one advantageous embodiment of the invention described by scheme S-1 and scheme S-A1, the duration of the hydrogenation reaction is between 0.5 and 10 h, preferably between 0.5 and 5 h and particularly preferably between 2 and 3 h.

b) Reductive Amination

In a second advantageous embodiment of the invention described by scheme S-2 and scheme S-A2, when the hydrogenation reaction has ended, the reaction medium is heated to a temperature Tb above the temperature Ta of step a) in order to initiate a reductive amination, said temperature advantageously being between 30 and 80° C., preferably between 40 and 60° C.

In one advantageous embodiment of the invention described by scheme S-2 and scheme S-A2, the reductive amination reaction is carried out at a hydrogen pressure of between 1 and 30 bar, preferably of between 5 and 15 bar.

In one advantageous embodiment of the invention according to scheme S-2 and scheme S-A2, the heating time is between 15 minutes and 5 hours, preferably between 30 minutes and 1 hour.

In one advantageous embodiment, the compound of formula (I) is isolated from the reaction medium and precipitated by spherical agglomeration according to the following steps:

a—filtration of the catalyst.

b—concentration of the medium.

c—addition of a quantity of water and an organic solvent (toluene) to the concentrate.

d—adjustment of the pH to a value of 6.3 (±0.3) by adding a strong base (NaOH).

e—separation of the aqueous phase and the organic phase.
f—addition of a volume of organic solvent (heptane) to the aqueous phase.
g—cooling of the medium at a temperature below 5° C. for 1 hour.
h—precipitation of the compound of formula (I) by adding a strong base (NaOH) until the pH is very basic, i.e. above 10.
i—filtration of the compound of formula (I) and drying under vacuum at a temperature of between 50 and 60° C., preferably at 55° C.

The compound of formula (II), and more specifically the compound of formula (II)A, is obtained by the processes described in the literature, such as that cited in patent number EP 112669 to Wyeth or that cited in patent number U.S. Pat. No. 5,043,466 to Wyeth.

Definitions

The above definitions apply to the description, the Example and the claims of the invention.

To facilitate understanding, the nomenclature of the groups, reactants, solvents or products is the international nomenclature or the nomenclature commonly used by those skilled in the art.

Other objects, characteristics and advantages of the invention will become clearly apparent from the following explanatory description including several Examples of the invention, which are given simply by way of illustration and cannot in any way limit the scope of the invention.

In the Examples, the percentages are given by weight, the temperature is room temperature or is given in degrees Celsius and the pressure is atmospheric pressure, unless indicated otherwise.

Furthermore, each Example forms an integral part of the invention and any characteristic that appears novel relative to any STATE OF THE ART forms an integral part of the invention and is claimed as such in its generality as a general means, and in its function.

EXAMPLE OF THE INVENTION

In situ or one-pot preparation of venlafaxine base: 1-[(2-dimethylamino)-1-(4-methoxyphenyl)ethyl]cyclohexanol (compound of formula (I) in which $R_1$=H, R2=OMe in the 4-position, R3=H, R4=H and n=1)

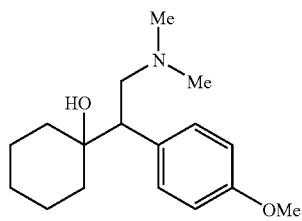

The following are placed in a Büchi reactor:
175 g (0.713 mol) of the product 1-[cyano(p-methoxyphenyl)methyl]cyclo-hexanol (compound of formula (II) in which $R_1$=H, R2=OMe in the 4-position, R3=H, R4=H and n=1);
52.5 g (0.0123 mol) of 5% palladium-on-charcoal with a moisture content of 50%;
47.1 g (1.57 mol) of paraformaldehyde pellets;
1050 ml of 100% acetic acid; and
700 ml of demineralized water.

a) Formation Reaction of Primary Amine by Hydrogenation
The medium is stirred and its temperature is adjusted to 5° C. for 30 min.
The reactor is placed under a hydrogen pressure of 12 bar.
The reaction medium is stirred at a temperature of between 5 and 15° C. for 3.5 h.

b) Reductive Amination Reaction
The reaction medium is then heated to a temperature of 60° C. and maintained at this temperature until the consumption of hydrogen has ceased.
The medium is cooled to a temperature of between 30 and 35° C.
The stirring is stopped and the pressure let down.
The reaction medium is withdrawn.
a) The catalyst is filtered off.
b) The filtrate is concentrated under vacuum until a stirrable viscous medium is obtained.
c) 350 ml of water are added and the medium is cooled to a temperature below 40° C. 175 ml of toluene are added to the medium, which is cooled to a temperature below 10° C.
d) The pH of the medium is adjusted to a value of 6.3±0.3 with 30% aqueous sodium hydroxide solution.
e) The medium is decanted and the aqueous phase is separated off. 175 ml of water are added to the toluene phase. The medium is stirred and the pH is adjusted to a value of 6.3±0.3 with 50% acetic acid. The medium is decanted and the aqueous phase is separated off.

The operation indicated in e) is repeated.
f) The aqueous phases are combined. 87.5 ml of heptane are added and the mixture is stirred for 5 min. The medium is decanted and the aqueous phase is separated off. A further 66.5 ml of heptane are added to the aqueous phase.
g) The medium is cooled to a temperature below 10° C.
h) 30% sodium hydroxide solution (105 ml) is added slowly to the medium in order to bring the pH to a value greater than or equal to 12.
i) The suspension is filtered. The isolated product is dried under vacuum at a temperature of 55° C. for 15 h.
KF analysis: 0.007% by weight The product is obtained with a yield of 93.8%. HPLC determination: 97.5% by weight.

The invention claimed is:
1. In situ or one-pot process for the preparation of a compound of general formula (I):

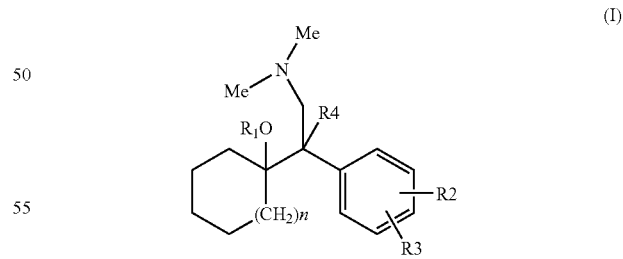

in which
$R_1$ is a hydrogen atom, a linear or branched $C_{1-6}$-alkyl, a fonnyl, a $C_{2-7}$-alkanoyl, a benzyl (—$CH_2C_6H_5$), a tetrahydrofitranyl, an alkylsilyl or arylsilyl, or a protective group for an oxygen atom, Gp;
R2 and R3 independently are a hydrogen atom, a linear or branched $C_{1-6}$-alkyl, a $C_{1-6}$-alkoxy (—OAk), a $C_{1-7}$-alkanoyloxy (—OC(O)Ak), a $C_{1-6}$-thioalkyl (—SAk), a halogen atom (Cl, Br, F), a trifluoromethyl (—$CF_3$), an "oxy" group where the oxygen atom is bonded to a protective group for the oxygen atom, or a substituted or unsubstituted $C_{6-10}$-aryloxy (—OAr), or R2 and R3 together form a methylenedioxy (—OR2R3O—);

R4 is a hydrogen atom or a linear or branched $C_{1-6}$-alkyl; and n is the integer 0, 1, 2, 3 or 4, the process comprising:

a) hydrogenation of a nitrile group of the compound of general formula (II):

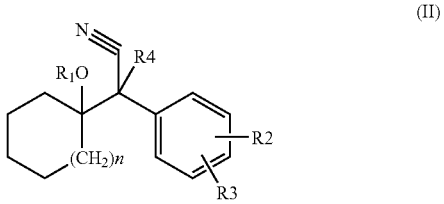

in which $R_1$, R2, R3, R4 and n are as defined above, in the presence of a hydrogenation catalyst, a methylating agent and an organic acid as solvent, and at a temperature Ta ranging between 5° C. and 25° C., to give a primary amine from the nitrile group; and b) reductive amination of the primary amine in the presence of hydrogen, at a temperature Tb of between 30° C. and 80° C., by, at the end of hydrogenation of step a), raising the temperature of the reaction medium to said temperature Tb to give the dimethylated amine of general formula (I) by activation of the methylating agent.

2. Process according to claim 1, wherein the compound of formula (I) is such that $R_1$ is a hydrogen atom, R2 is a methoxy group in the para position, R3 and R4 are a hydrogen atom and n is equal to 1.

3. Process according to claim 1, wherein the hydrogenation catalyst is a supported or unsupported catalyst based on palladium, platinum or nickel.

4. Process according to claim 1, wherein the hydrogenation catalyst is palladium supported on carbon (Pd/C).

5. Process according to claim 1, wherein the organic acid used as solvent is acetic acid.

6. Process according to claim 1, wherein the acetic acid is pure or in aqueous solution.

7. Process according to claim 1, wherein the methylating agent used is selected from formaldehyde, paraformaldehyde, a linear polyoxymethylene, a cyclic polyoxymethylene and polyoxymethylene diacetates.

8. Process according to claim 1, wherein the methylating agent used is paraformaldehyde in a solid form, e.g. in the form of pellets.

9. Process according to claim 1, wherein the hydrogenation reaction is carried out at a temperature Ta of between 5° C. and 15° C.

10. Process according to claim 1, wherein the amount of catalyst used relative to the product is between 1/1000 and 1/10, expressed in mol of metal/mol of product.

11. Process according to claim 1, wherein the hydrogenation is carried out at a hydrogen pressure of between 1 bar and 30 bar.

12. Process according to claim 1, wherein when the hydrogenation has ended, the reaction medium is heated to a temperature Tb of between 40° C. and 60° C.

13. Process according to claim 1, wherein the reductive amination is carried out at a hydrogen pressure of between 1 bar and 30 bar.

14. Process according to claim 1, wherein the reductive amination is carried out over a period of between 15 minutes and 5 hours.

15. In situ or one-pot process for the preparation of a compound of general formula (I):

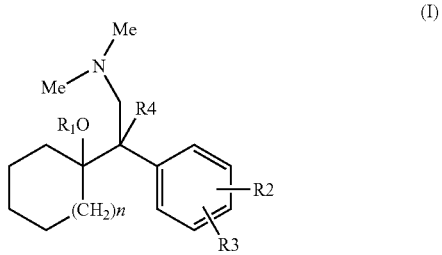

in which

R1 is a hydrogen atom, a linear or branched $C_{1-6}$-alkyl, a formyl, a $C_{2-7}$-alkanoyl, a benzyl (—CH$_2$C$_6$H$_5$), a tetrahydrofuranyl, an alkylsilyl or arylsilyl, or a protective group for an oxygen atom, Gp;

R2 and R3 independently are a hydrogen atom, a linear or branched $C_{1-6}$-alkyl, a $C_{1-6}$-alkoxy (—OAk), a $C_{1-7}$-alkanoyloxy (—OC(O)Ak), a $C_{1-6}$-thioalkyl (—SAk), a halogen atom (Cl, Br, F), a trifluoromethyl (—CF$_3$), an "oxy" group where the oxygen atom is bonded to a protective group for the oxygen atom, or a substituted or unsubstituted $C_{6-10}$-aryloxy (—OAr), or R2 and R3 together form a methylenedioxy (—OR2R3O—);

R4 is a hydrogen atom or a linear or branched $C_{1-6}$-alkyl; and n is the integer 0, 1, 2, 3 or 4, the process comprising:

a) hydrogenation of a nitrile group of the compound of general formula (II):

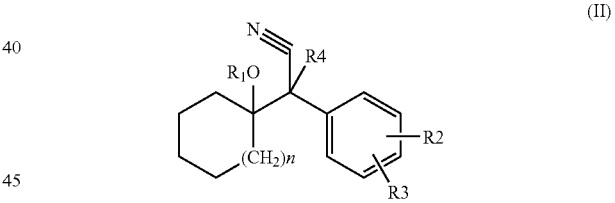

in which $R_1$, R2, R3, R4 and n are as defined above, in the presence of a hydrogenation catalyst; a methylating agent selected from formaldehyde, paraformaldehyde, a linear polyoxymethylene, a cyclic polyoxymethylene, and polyoxymethylene diacetate; and an organic acid as solvent; and at a temperature Ta ranging between 5° C. and 25° C., to give a primary amine from the nitrile group; and b) reductive amination of the primary amine in the presence of hydrogen, at a temperature Tb of between 30° C. and 80° C., by, at the end of hydrogenation of step a), raising the temperature of the reaction medium to said temperature Tb to give the dimethylated amine of general formula (I) by activation of the methylating agent.

16. The method of claim 15, wherein the cyclic polyoxymethylene is selected from 1,3,5-trioxane and 1,3,5,7-tetraoxane.

* * * * *